(12) United States Patent
Giphart et al.

(10) Patent No.: US 7,810,996 B1
(45) Date of Patent: Oct. 12, 2010

(54) DUAL FLUOROSCOPY SYSTEMS AND METHODS

(75) Inventors: Johan Erik Giphart, Edwards, CO (US); Michael Ray Torry, Edwards, CO (US); Kevin Barry Shelburne, Golden, CO (US)

(73) Assignee: Steadman Philippon Research Institute, Vail, CO (US)

( * ) Notice: Subject to any disclaimer, the term of this patent is extended or adjusted under 35 U.S.C. 154(b) by 0 days.

(21) Appl. No.: 12/022,063

(22) Filed: Jan. 29, 2008

Related U.S. Application Data

(60) Provisional application No. 60/887,130, filed on Jan. 29, 2007.

(51) Int. Cl.
*G01D 18/00* (2006.01)

(52) U.S. Cl. ...................................... 378/207; 378/205

(58) Field of Classification Search ................ 378/205, 378/207, 197–198, 62
See application file for complete search history.

(56) References Cited

U.S. PATENT DOCUMENTS

| | | | | |
|---|---|---|---|---|
| 6,104,780 | A * | 8/2000 | Hanover et al. | 378/92 |
| 2003/0014034 | A1 * | 1/2003 | Strobel | 604/407 |
| 2004/0066906 | A1 * | 4/2004 | Hornegger et al. | 378/197 |
| 2005/0281384 | A1 * | 12/2005 | Cho et al. | 378/156 |

OTHER PUBLICATIONS

Banks, et al., "Accurate Measurement of Three-Dimensional Knee Replacement Kinematics Using Single-Plane Fluoroscopy," IEEE Transactions on Biomedical Engineering, vol. 43, No. 6, pp. 638-649 (Jun. 1996).
Komistek, et al., "In Vivo Fluoroscopic Analysis of the Normal Human Knee," Clinical Orthopaedics and Related Research, No. 410, pp. 69-81 (May 2003).
Dennis, et al., "In vivo determination of normal and anterior cruciate ligament-deficient knee kinematics," Journal of Biomechanics, vol. 38, pp. 241-253 (2005).

(Continued)

*Primary Examiner*—Hoon Song
(74) *Attorney, Agent, or Firm*—Faegre & Benson LLP

(57) ABSTRACT

A method for constructing a dual fluoroscopy system according to embodiments of the present invention includes providing a first c-arm and a second c-arm, each of which include an x-ray generator and an imaging device, synchronizing exposure timing of the two x-ray generators, decoupling the x-ray generators from the imaging devices and mounting them on a gantry system, aligning one x-ray generator with an imaging device and aligning the other x-ray generator with the other imaging device, and performing a calibration test to determine the dual fluoroscopy system configuration, and attaching a triggering and visualization device. An imaging system of the imaging device may be upgraded to permit faster data capture rates, according to embodiments of the present invention.

26 Claims, 11 Drawing Sheets

OTHER PUBLICATIONS

Ramsey, et al., "Methodological concerns using intra-cortical pins to measure tibiofemoral kinematics," Knee Surg Sports Traumatol Arthrosc., vol. 11, pp. 344-349 (2003).

Mahfouz, et al., "In Vivo Determinantion of Knee Kinematics in Patients with a Hamstring or Patellar Tendon ACL Graft," Journal of Knee Surgery, vol. 16, No. 4, pp. 197-202 (Oct. 2003).

Tashman, et al., "Abnormal rotational knee motion during running after anterior cruciate ligament reconstruction," American Journal of Sports Medicine, vol. 32, No. 4, pp. 975-983 (2004).

You, et al., "In vivo measurement of 3-D skeletal kinematics from sequences of biplane radiographs: application to knee kinematics," IEEE Transactions on Medical Imaging, vol. 20, No. 6, pp. 514-525 (Jun. 2001).

Tashman, et al., "In-Vivo Measurement of Dynamic Joint Motion Using High Speed Biplane Radiography and CT: Application to Canine ACL Deficiency," Journal of Biomechanical Engineering, vol. 125, pp. 238-245 (Apr. 2003).

* cited by examiner

DUAL FLUOROSCOPY SYSTEMS AND METHODS

CROSS-REFERENCE TO RELATED APPLICATION

This application claims the benefit of U.S. Provisional Patent Application Ser. No. 60/887,130, filed Jan. 29, 2007, which is herein incorporated by reference in its entirety.

TECHNICAL FIELD

Embodiments of the present invention relate generally to kinematic observation and measurement of living bones and tissue, as well as implanted objects, and more specifically to dual fluoroscopy systems and methods.

BACKGROUND

Accurate three-dimensional (3D) visualization, measurement and tracking of the location and motion (kinematics) of structures (e.g., organs, bones, markers, tools, implanted hardware, contrast agents, etc.) inside the body is important to many fields in medicine. Currently, many details of motions inside the body are unknown because systems are limited by their: ability to produce images in only two dimensions (2D), poor image resolution, slow imaging speed, and restriction on patient mobility.

Traditionally, joint motion has been measured using video-based systems that record the location of reflective markers placed on the skin while the subjects perform activities such as walking, running, rehabilitation exercises or even throwing a ball. However, the motion of the skin and underlying soft tissues does not always reflect the motion of the bones and the joints moving beneath them. For this reason, such systems may not provide the accuracy needed to measure small but clinically significant changes in joint motion. Even attaching the reflective markers to pins surgically inserted into the bones directly may result in joint kinematic errors of 2-4 mm, as others have found, far higher than the sub-millimeter accuracy necessary to measure crucial changes in joint motion. For instance, the difference between two surgical knee-ligament reconstruction techniques may be less than 1 mm of translation during walking; yet this small difference may contribute to the development of osteoarthritis after one surgical technique but not the other.

In the field of cardiac imaging, low frame rates limit the visualization of the dynamic details of the pumping heart, the fluid dynamics of the blood entering and being ejected from the heart's chambers, the flow of the blood through the coronary arteries, and/or the dynamic distention and motion of the coronary arteries during the heart beat. The ability to visualize these motions as well as measure and track the dynamic motions occurring during the heart beat may lead to improved diagnosis and treatment of heart and coronary diseases. Similarly, in the field of oncology and surgery, accurate guiding of the treatment radiation beam or surgical instrument inside the body such as the brain can mean the difference between a successful treatment and potential complications. In many other fields of medicine, the ability to visualize, track and guide, in 3D, structures and instruments internal to the body will make a significant difference in the diagnosis and treatment of disease.

SUMMARY

Methods for constructing a dual fluoroscopy system according to embodiments of the present invention include providing a first c-arm and a second c-arm, each of which include an x-ray generator and an imaging device, synchronizing exposure timing of the two x-ray generators, decoupling the x-ray generators from the imaging devices, aligning one x-ray generator with an imaging device and aligning the other x-ray generator with the other imaging device, and performing a calibration test of the imaging devices to measure and correct image distortion and to determine the relative positions and orientations of the system components. Methods according to embodiments of the present invention may further include mounting the first x-ray generator to a first gantry, the second x-ray generator to a second gantry, the first imaging device to a third gantry, and the second imaging device to a fourth gantry, such that the gantries move independently and include height and position adjustment features. Methods according to embodiments of the present invention may further include attaching a triggering and beam visualization device. Methods according to embodiments of the present invention may also include an imaging speed upgrade to the imaging devices to permit faster data acquisition.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
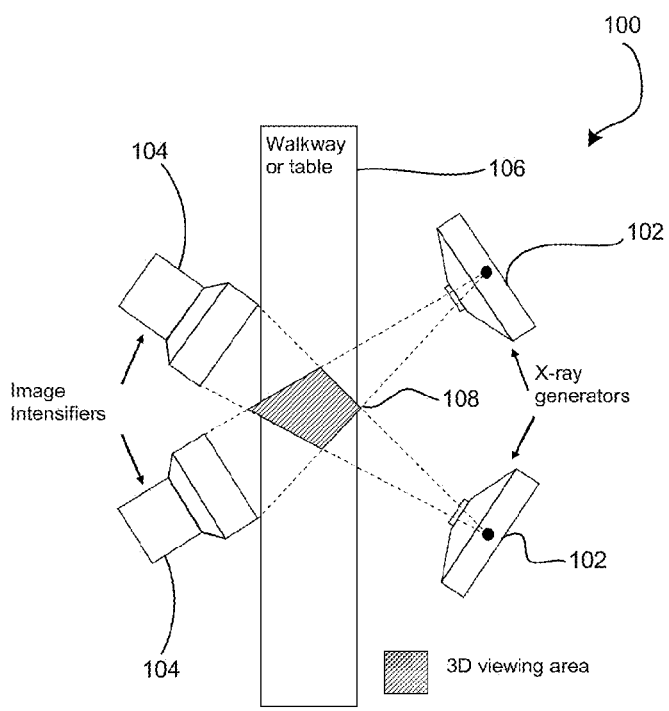
FIG. 1 illustrates a top view of a schematic layout of a dual fluoroscopy system, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In recent years, some techniques have been developed that use fluoroscopy to measure the motion of structures and objects inside the body (e.g., bones or implants) directly in vivo and during activity. Kinematic measurements with accuracies of better than one millimeter may be possible using computer-guided registration techniques that map three-dimensional object geometries obtained from computed tomography (CT) or computer aided design (CAD) models to two-dimensional fluoroscopic projection images, as others have found. While these techniques can be applied using a single fluoroscopy system, the out-of-plane motions often have poor accuracy and may be measured no better than using a video-based or other motion analysis system.

Due to regulatory requirements, ease-of-use, and other considerations, current single fluoroscopy systems are often manufactured and sold with an arm which couples a single radiation generator to a single imaging device. The radiation generator is often coupled with the imaging device by a C-shaped arm; therefore, such single fluoroscopy systems are often referred to as c-arms. As used herein, the term "c-arm" is used to refer to a single fluoroscopy system with a single x-ray generator and a single imaging device connected by an arm. One example of a c-arm is a twelve-inch BV Pulsera Release 2, Mobile X-ray Unit from Philips Medical Systems, part number NMCA107. The coupling arm in a c-arm may include numerous configurations; for example, it may be curved, segmented, L-shaped, and/or J-shaped. The c-arm configuration permits only a relatively fixed distance between the x-ray generator and the imaging device, which significantly limits the degree of movement that may be made by a living patient between the x-ray generator and the imaging device.

Existing biplane radiography systems are often constructed "from scratch," and often at great expense and complexity. Commercial biplane neurovascular systems exist (for example, the Philips Allura Xper FD20/10 or the Philips Allura 3D-RA), but are often very large, ceiling-mounted operating room systems which are very expensive, on the order of one to two million U.S. dollars. Dual fluoroscopy systems according to embodiments of the present invention, however, can be made by purchasing a pair of existing, "off-the-shelf" c-arms, and then modifying, calibrating, and synchronizing them as described herein, according to embodiments of the present invention. Separating the x-ray generators and imaging devices from the c-arms and mounting them on their own gantry system, as well as synchronizing the two single fluoroscopy systems, permits observation and study of a wider, more complete range of motion for an observed body structure in a relatively cost effective manner.

While embodiments of the present invention may be used to measure any structure or object inside the body performing any motion (see non-limiting examples below), the following description relates to measuring motion in the knee joint. The anterior cruciate ligament (ACL) is the most frequently injured ligament within the knee. ACL injury affects roughly one in 3,000 people each year in the United States. The incidence is much higher in certain segments of the athletic population such as football players and skiers. Recently, it has been documented that females injure their ACL two to eight times more frequently than their male counterparts in similar sports activities. Some authors have described this alarming injury rate as an epidemic. For most patients, ACL reconstruction is the mainstay of treatment for knee instability following this injury. As data from long-term follow-up suggests, there are unsatisfactory results in 15-25% of the patients, and revision ACL reconstruction has become a very significant and difficult problem to address. In addition, some studies found that five years after surgery there was a higher instance of degenerative joint disease in patients who underwent ACL reconstruction.

Forces and deformations of the ACL and ACL replacement grafts have been measured in cadaveric and animal knee specimens in many laboratories. All such investigations have advanced the field, taught the field more about the complex function of the ACL, and provided insight into improving ACL reconstruction. However, because such data are based on animal or cadaveric studies, such investigations may not accurately portray how living tissues behave during real human activity (in vivo). Thus, the most exciting and clinically relevant data are those measured in the ACL of living volunteers and patients as they conduct various activities of daily living and exercises. Therefore, embodiments of the present invention may be used to compare the bony motions in the knee between healthy knees, knees with ruptured ACLs, and knees with reconstructed ACLs using two different grafting techniques (bone-patella tendon-bone graft or hamstring graft) during walking and the performance of rehabilitation exercises.

Embodiments of the present invention measure object motion by using two fluoroscopy systems at an angle relative to each other. According to embodiments of the present invention, such a dual fluoroscopy system 100 is a high-resolution dual fluoroscopy system. FIG. 1 illustrates a schematic layout of a dual fluoroscopy system 100 as viewed from above. Two fluoroscopy systems are positioned at an angle with respect to each other to correct for potentially significant out-of-plane error for each individual fluoroscopy system, according to embodiments of the present invention.

The system 100 includes two x-ray generators 102 and two imaging devices 104, according to embodiments of the present invention. The x-ray beams intersect to form a three-dimensional field of view 108. A walkway or table and/or the like 106 may be included to permit walking, running, or other motion to be performed and observed within the field of view 108, according to embodiments of the present invention. Some examples of imaging devices 104 include: an image intensifier with an attached camera, and a flat detector (for example, the Philips Flat Detector), according to embodiments of the present invention.

General System Components

Use of embodiments of the present invention is not limited to a specific object or a specific motion and, therefore, embodiments of systems according to the present invention allow for maximum flexibility both in the objects that can be imaged, as well as the motions that can occur inside the body or that can be performed by the patients. In case of orthopedics, of particular interest may be motions that challenge joints as these motions are typically fast and of high frequency content. Therefore, fast shutter speeds and high frame rates may facilitate the recording of these motions, respectively. As a result of these goals, some desired specifications according to embodiments of the present invention are:

Two fluoroscopy systems for true three-dimensional motion recording that have coupled control systems so that the radiation exposures, whether pulsed or continuous, are accurately timed relative to each other.

A gantry that allows for variable source to image distance (SID; source generator to image plane distance) of 1.0-2.0 meters, as well as variable configurations between the fluoroscopy systems and between the systems and the patient to allow for the ability to optimize viewing volume, movement freedom and technique factors.

Two coupled high-speed cameras with frame rates of 60 frames per second or higher that are interfaced with the image intensifiers of the fluoroscopy systems (or other imaging devices such as flat detectors capable of recording at high frame rates). Shutter speeds of 1/2000 s or higher (such that motion blur at 2 m/s≦1 mm) are desirable in most cases.

Accurate calibration methods that are used to: 1) correct for the image distortion of the imaging devices, and 2) determine the focus position of each generator relative to its corresponding imaging device, and 3) that can accurately determine the geometric relationship between the two fluoroscopy systems.

A triggering and beam visualization device to be used to trigger and visualize the x-ray generation, which in some cases may be used to trigger and visualize the x-ray generation based on events detected by sensors.

Subjects can walk, run, jump through the system as well as throw a ball and perform rehabilitation exercises using weights and elastic cords, according to embodiments of the present invention.

Other desired specifications may differ according to other embodiments of the present invention.

Figure 2:
FIG. 2 illustrates an experimental setup example using two standard operating room fluoroscopy units during a pilot experiment designed to measure motion in a cadaver knee, according to embodiments of the present invention.

FIG. 2 illustrates an experimental setup example using two standard operating room fluoroscopy units during a pilot experiment designed to measure motion in a cadaver knee. In some cases, freedom of movement in the viewing area in front of the image intensifiers may be very limited, as shown in FIG. 2.

The biplane fluoroscopy system can be built from components or created by modifying standard fluoroscopy systems. Standard c-arm fluoroscopy units used in operating rooms have: a fixed SID of approximately 100 cm, c-arms of approximately the same diameter that can be rotated around 2 axes and are mounted on wheels, and a maximum image capture rate of 30 frames per second. Therefore, such fluoroscopy units may be modified in three ways, according to embodiments of the present invention:

the control systems of two standard systems may be coupled so that the radiation exposures, whether pulsed or continuous, are accurately timed relative to each other, the c-arms, which are overly restrictive in most applications, may be replaced with more flexible and less obtrusive gantries, and the image acquisition systems of the fluoroscopy units, which are too slow for some applications, may be replaced with high-resolution and/or high-frame rate image acquisition systems.

Description of Hardware Design

Coupling of Exposure Control Systems

According to some embodiments of the present invention, a dual fluoroscopy system for object measurement may be built by first acquiring two fully operational c-arms (e.g. GE OEC 9800; Philips Pulsera; Siemens ARCADIS) and modifying these systems in a staged fashion, or by acquiring the x-ray generator components and imaging device components independently. Coupling the control systems may enhance the accurate timing of the radiation exposures, whether pulsed or continuous, and the corresponding image acquisitions relative to each other. According to embodiments of the present invention, this involves understanding and coordinating knowledge of the control signals within the x-ray generator as well as the imaging system and the appropriate sequencing of these signals to synchronize the exposures. Pulsed exposures can be organized so that the pulses in each system alternate or are simultaneous. Simultaneous exposures simplify the analysis because the two images are taken with the object in exactly the same location, according to embodiments of the present invention. However, simultaneous exposures may decrease the image quality by increasing x-ray noise due to scatter from the x-ray beam of one fluoroscopy unit to the imaging device of the other fluoroscopy unit. In case of building the system from components, a gantry is helpful in using the system which is described below. In case of the modification of two 30 fr/s fluoroscopy units, such a modification may permit immediate study of simple, slow motions with a setup similar to that shown in FIG. 2.

Using the pulsed fluoroscopy modes available on the systems, subject exposure may be minimized while allowing researchers to gain valuable experience using such systems. Even though patient freedom of movement may be limited by such a setup in some cases, it may allow researchers to adequately prepare for the modification stages described below while being scientifically productive from the start.

Figure 13:
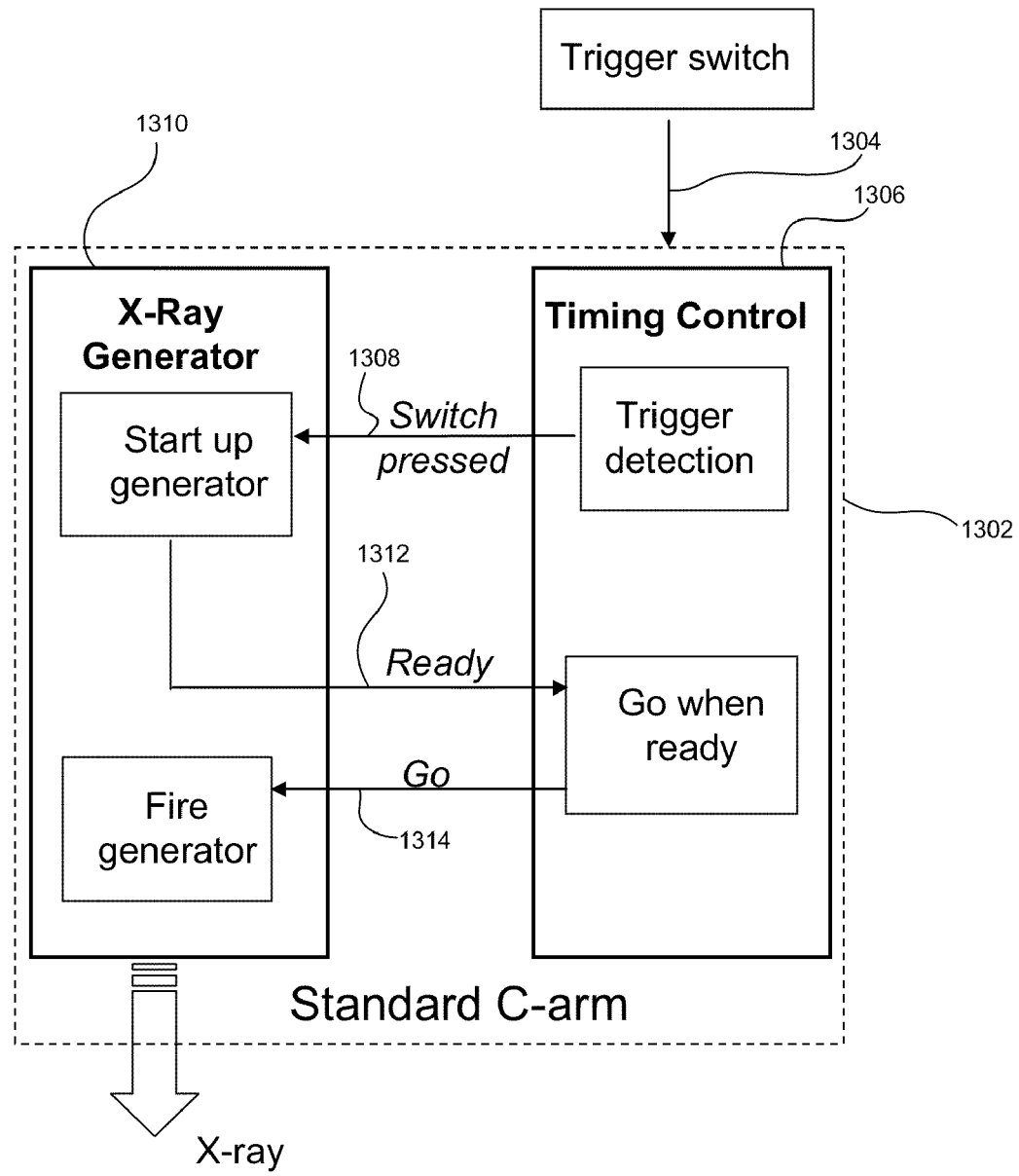
FIG. 13 illustrates a system signaling diagram for a typical c-arm, according to embodiments of the present invention.

FIG. 13 illustrates a timing control signaling diagram in a typical c-arm single fluoroscopy unit, according to embodiments of the present invention. A trigger switch sends a trigger signal 1304 to the system control module 1302. System control module 1302 includes a timing control module 1306 and an x-ray generator control module 1310, according to embodiments of the present invention. As described above, the trigger signal 1304 may be sent by a simple manual button or by a triggering device that combines signals from a manual button and/or the alignment photocells 802 and/or a motion sensing switch, according to embodiments of the present invention. The trigger signal 1304 may be produced when one or more conditions have been satisfied. Optionally, the safety switches related to the alignment photocells 802 and manual button may be located elsewhere in the system controls 1302 to prevent firing of the x-ray generator 102 in an unsafe condition, according to embodiments of the present invention.

The timing control module 1306 receives the trigger signal 1304, and in response sends a generator startup signal 1308 to the x-ray generator module 1310. The x-ray generator module 1310 starts up the x-ray generator 102 and, when the x-ray generator 102 is ready to fire, the x-ray generator control module 1310 sends a ready indication signal 1312 back to the timing control module 1306. The timing control module 1306 receives the ready indication signal 1312 and sends the x-ray generator control module 1310 a "go" signal 1314. The x-ray generator control module 1310 receives the "go" signal 1314 and, in response, fires the x-ray generator 102, according to embodiments of the present invention.

Figure 14:
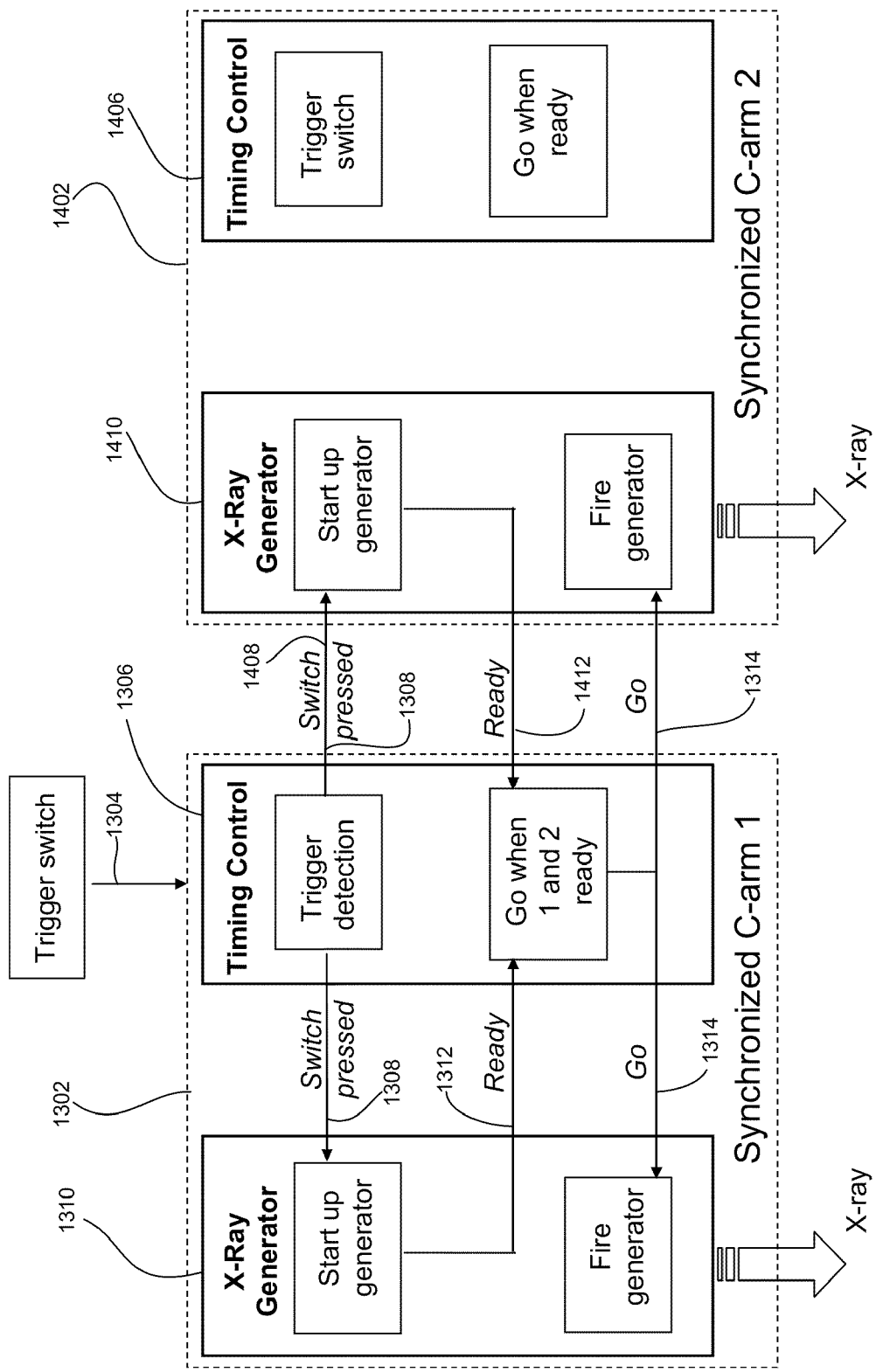
FIG. 14 illustrates a system signaling diagram for two linked and synchronized c-arms, according to embodiments of the present invention.

FIG. 14 illustrates a timing control signaling diagram for two c-arm single fluoroscopy units that have been synchronized, according to embodiments of the present invention. The control systems 1302, 1402 may be implemented in hardware, in software on a computer system, or a combination of both, according to embodiments of the present invention. The timing control module 1306 receives the trigger signal 1304, and in response sends a generator startup signal 1308 to the x-ray generator module 1310 and also to the x-ray generator control module 1410 of the control system 1402 of the second c-arm. Alternatively, the trigger signal 1304 may be sent simultaneously to the timing control unit 1406 of control system 1402, and in response, timing control unit 1406 sends the switch-pressed signal 1408 to x-ray generator module 1410. The x-ray generator modules 1310, 1410 then start up their respective x-ray generators 102 and, when the x-ray generator 102 of the first c-arm control system 1302 is ready to fire, the x-ray generator control module 1310 sends a ready indication signal 1312 back to the timing control module 1306. When the x-ray generator 102 of the second c-arm control system 1402 is ready to fire, the x-ray generator control module 1410 sends a ready indication signal 1412 back to the timing control module 1306. Because the x-ray generators 102 attached to either of the x-ray control modules 1310, 1410 may take different periods of time to warm up and/or start up, the timing control module 1306 waits until both ready signals 1312, 1412 are received before simultaneously sending a "go" signal 1314 to both x-ray generator control 1310 and x-ray generator control 1410, according to embodiments of the present invention. When the "go" signals 1314 are received, both x-ray generator controls 1310, 1410 fire their x-ray generators 102 simultaneously, according to embodiments of the present invention. Based on the disclosure provided herein, one of ordinary skill in the art will appreciate the numerous different ways in which the control systems 1302, 1402 of two stand-alone c-arms may be linked and synchronized, according to embodiments of the present invention.

Gantry Design

Figure 3:
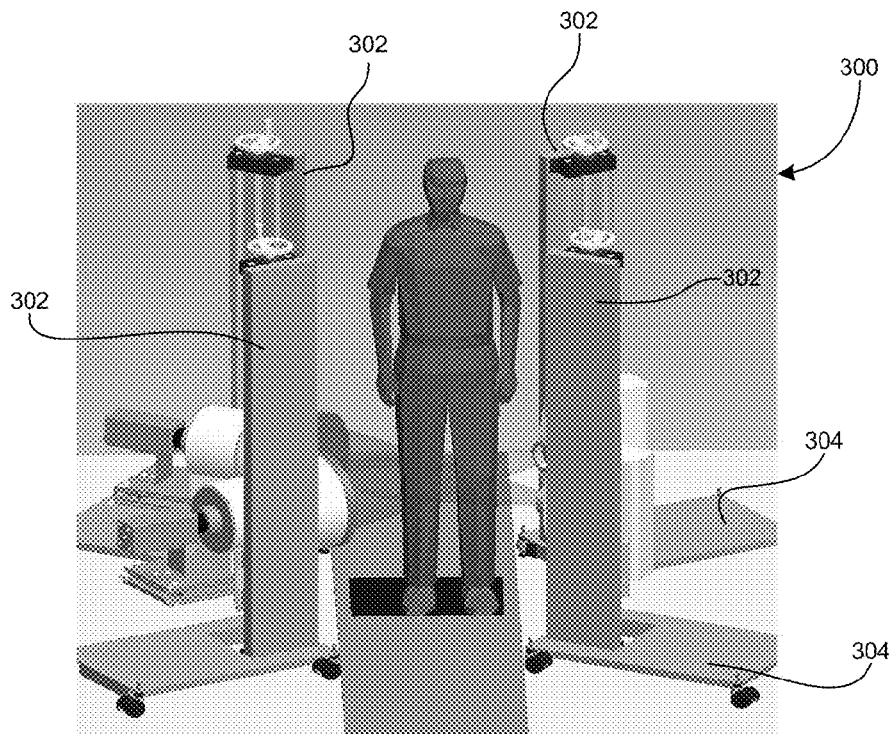
FIG. 3 depicts a rendering of a dual fluoroscopy system imaging a knee, according to embodiments of the present invention.
Figure 4:
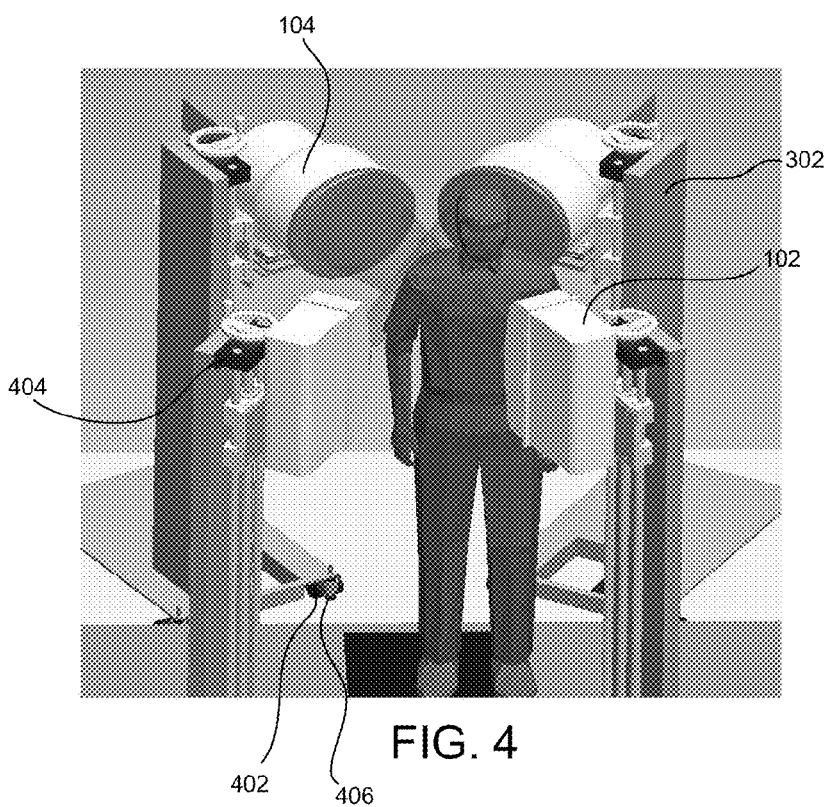
FIG. 4 depicts a rendering of a dual fluoroscopy system imaging a shoulder, according to embodiments of the present invention.

According to some embodiments of the present invention, an additional modification includes removing the x-ray generators and imaging devices from the c-arm ends and attaching them to a new gantry system, as shown in FIGS. 3 and 4. A gantry system 300 according to embodiments of the present invention may consist of four towers 302 on wheels 402 with adjustable feet 406 that can be lowered to the ground rendering the towers 302 stationary. Each tower 302 may consist of a base 304 and a lifting mechanism 404 that will allow the attached x-ray generator 102 and/or imaging device 104 to be moved vertically from the level of the ankle up to the height of the neck of an average adult human patient. Such a gantry design gives subjects significantly more freedom of movement, even when the source to image distance is not changed, according to embodiments of the present invention. FIG. 3 depicts a rendering of a dual fluoroscopy system imaging a knee, and FIG. 4 depicts a rendering of a dual fluoroscopy system imaging a shoulder, according to embodiments of the present invention. The gantry mechanism 300 and 302 allows freedom of movement while imaging from the height of the ankle to the neck, according to embodiments of the present invention.

Horizontal Alignment and Perpendicular Positioning

Figure 5:
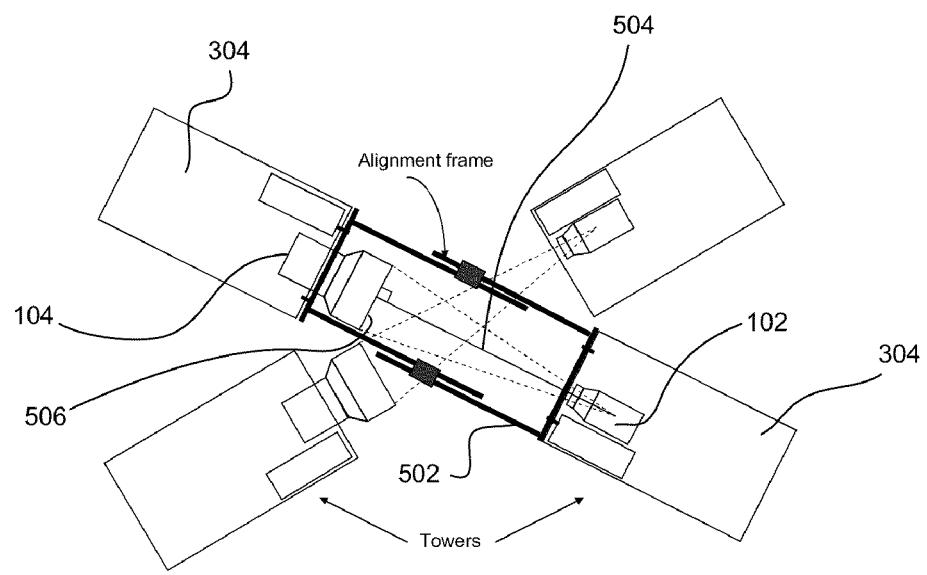
FIG. 5 illustrates a top view schematic design of an alignment frame, according to embodiments of the present invention.

Potentially applicable government regulations may specify that the x-ray beam and imaging surface are centered and perpendicular at all times and that the x-ray beam is intercepted by the system at all times. FIG. 5 illustrates a schematic design of an alignment frame 502 viewed from above. The frame helps to center the x-ray beam 504 horizontally and helps to ensure that the beam 504 is perpendicular to the imaging surface 506, according to embodiments of the present invention. An alignment frame 502, which may be firmly attached (e.g. bolted) to the bases 304 of the towers 302 containing an x-ray generator 102 on one side and a corresponding imaging device 104 on the other side, may be used to align the two opposing components horizontally while their adjustable feet are in a raised position. This alignment mechanism centers the x-ray beam horizontally and helps to ensure that the imaging device 104 is perpendicular to the beam 504. According to some embodiments of the present invention, the alignment frame 502 ensures that the x-ray beam 504 is perpendicular to the image plane 506 to within +/−3 degrees. The alignment frame 504 may include two slidably coupled components to permit alignment of the bases 304 of towers 302 at varying source-to-image distances, according to embodiments of the present invention.

Figure 6:
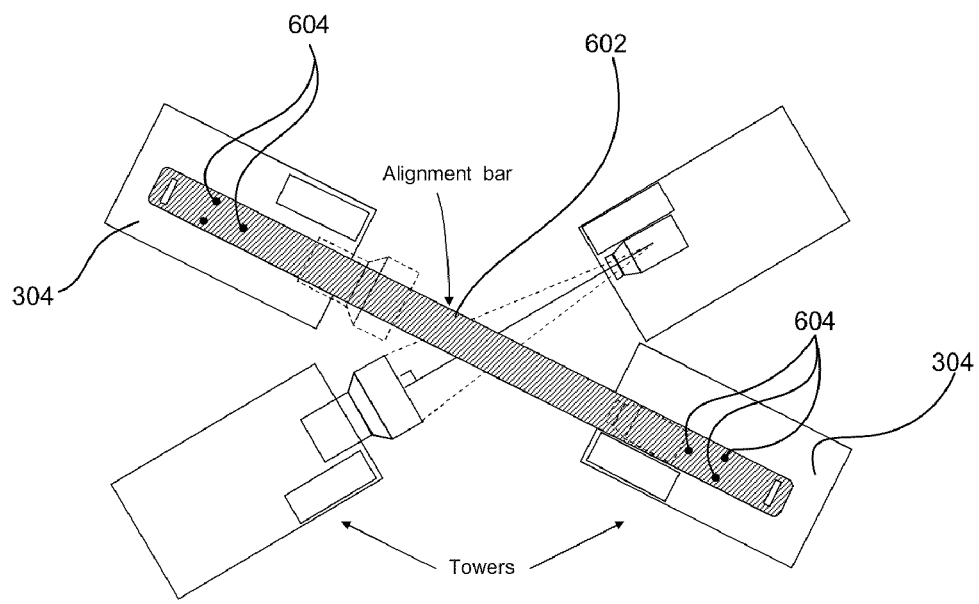
FIG. 6 illustrates a top view schematic design of an alignment bar, according to embodiments of the present invention.

FIG. 6 illustrates an alternative alignment mechanism, according to embodiments of the present invention. An alignment bar 602 may be bolted to the bases 304 of opposing gantry towers 302 at bolt locations 604, according to embodiments of the present invention. According to some embodiments of the present invention, the adjustable feet 406 may be raised such that the base 304 rolls on the wheels 402. Then, the alignment frame 502 and/or the alignment bar 602 may be coupled from one base 304 to another 304 to perform the alignment operation. Finally, the adjustable feet 406 may be lowered to raise the wheels 402 and secure the bases 304 in a relatively fixed position with respect to an underlying surface, and the alignment frame 502 and/or bar 602 may be removed. The adjustable feet 406 may be used to level the base 304 accurately according to leveling indicators (not shown) attached to the base 304, according to embodiments of the present invention.

Vertical Alignment

Figure 7:
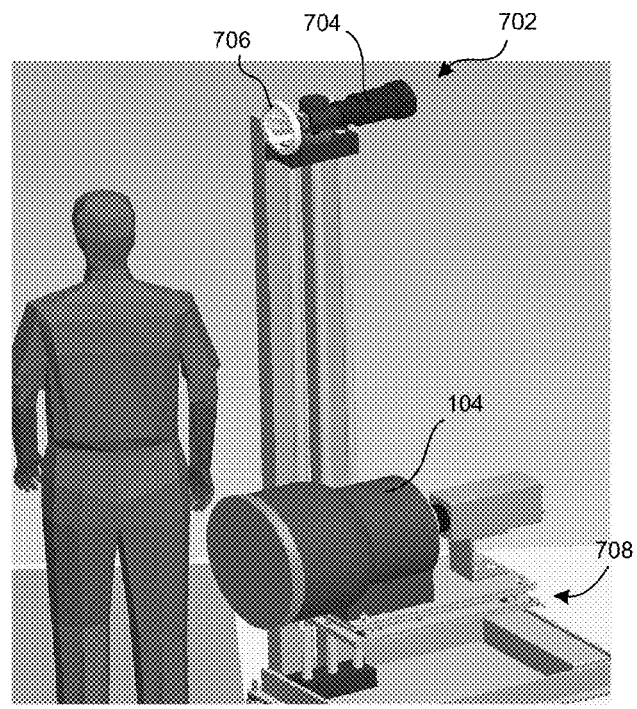
FIG. 7 illustrates a front view of a vertical lifting mechanism for adjustment of the height of the generator and imaging devices, according to embodiments of the present invention.

FIG. 7 depicts a lifting mechanism 702 which can be manually operated by, for example, a hand crank 706, or which can be automatically operated by, for example, a motor 704, according to embodiments of the present invention. The lifting mechanism 702 may include a vertical screw and slider assembly driven by either the hand wheel 706 or motor 704 to raise and lower a platform 708 on which the imaging device 104 or x-ray generator 102 is positioned, according to embodiments of the present invention. The lifting mechanism 702 positions the generator assembly 102 and imaging assembly 104 either together simultaneously or independently at the desired height, according to embodiments of the present invention. The vertical alignment of the x-ray generator 102 and imaging device 104 may be confirmed using one or more photocells 802 with sensors attached to the x-ray generator 102 and reflectors 804 on the imaging assembly 104 or vice versa, according to embodiments of the present invention. Alternatively, lasers may be attached to the x-ray generators 102 and photodiodes may be attached to the imaging devices 104, or vice versa.

Figure 8:
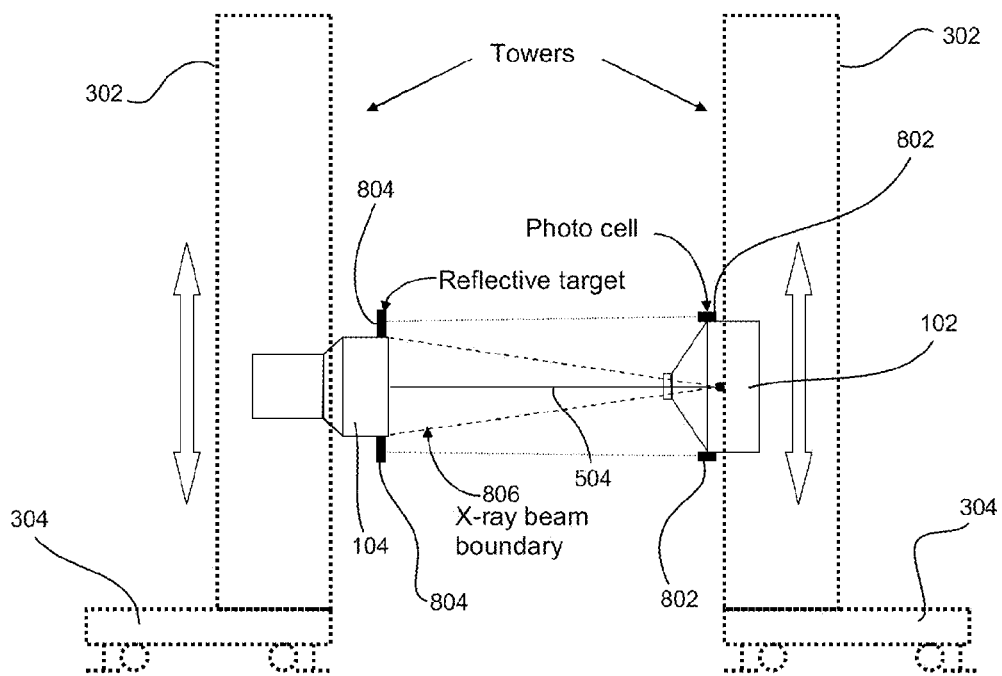
FIG. 8 illustrates a schematic design of the horizontal and/or vertical alignment of the x-ray beam with the imaging device using photo cells, according to embodiments of the present invention.

FIG. 8 illustrates a schematic design of the vertical alignment of the x-ray beam 504 with the image intensifier 104 using photo cells 802. By including the one or more photocells 802 in the electronic triggering circuitry of the x-ray generator 102, the x-ray generator 102 may be configured to activate only when the two assemblies 102, 104 are properly vertically and/or horizontally positioned, so that the imaging device 104 may perform its primary barrier function, according to embodiments of the present invention. The imaging device 104 performs its primary barrier function when no part of the x-ray beam boundary 806 is transmitted outside of the imaging device 804, according to embodiments of the present invention. Using three or more photocell 802 and reflector 804 pairs enables the confirmation of both vertical and horizontal alignment, according to embodiments of the present invention. According to some embodiments of the present invention, a laser and photodiode combination may be used instead of a photocell 802 and reflector 804 combination, for improved accuracy.

Alignment and Positioning

Figure 9:
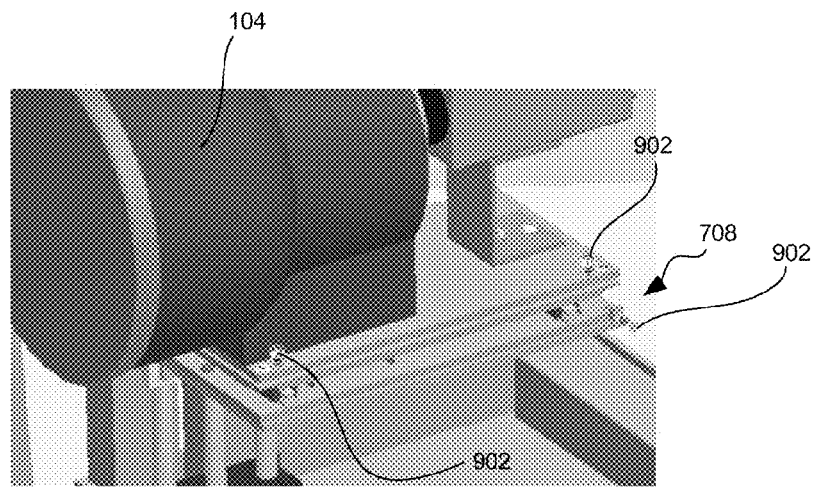
FIG. 9 illustrates a fine adjustment platform for precise alignment of the x-ray beam to the imaging system, according to embodiments of the present invention.

FIG. 9 illustrates a fine adjustment platform for precise alignment of the x-ray generator to the imaging system. The four degree of freedom table 708 allows fine adjustment of yaw-pitch-roll and horizontal translation in the imaging plane, by manipulation of set screws 902, according to embodiments of the present invention. According to embodiments of the present invention, during installation and later when needed, smaller adjustments to the position of the x-ray generator 102 and/or imaging device 104 can be made using a four degree-of-freedom adjustment table located on the x-ray generator 102 and/or on the imaging system 104. These adjustments may more precisely align the x-ray generators 102 and imaging systems 104 for the purpose of both radiation safety and imaging accuracy, according to embodiments of the present invention. A simpler two-dimensional adjustment system for pitch and yaw may be placed on the x-ray generator 102 and/or on the imaging system 104, according to embodiments of the present invention. According to some embodiments of the present invention, the four degree of freedom table 708 is used on the x-ray generator 102 side, because small angular changes in the x-ray beam often result in larger displacements at the imaging device 104.

Variable Source to Image Distance (SID)

The ability to adjust the source to image distance permits optimization of the viewing volume, its location and the amount of motion freedom the subject needs to perform the task to be imaged. According to some embodiments, only a handful of discreet SIDs may be implemented, in which case an x-ray beam dimensional restriction of 2% may be implemented by using an assortment of removable, fixed-aperture, beam-limiting devices for each source to image distance. Alignment frame 502 or bar 602 as well as the beam-limiting device may include clearly visible markings to indicate the current source to image distance; if the purchased c-arm provides more sophisticated collimation options (e.g., stepless collimation), such options may be used instead of the removable, fixed-aperture, beam-limiting devices.

Primary Barrier

According to some embodiments of the present invention, the imaging device 104 may serve as the primary protective barrier. According to such embodiments, the alignment and collimation procedure described above serves to maintain the useful beam within the limits of the image intensifier or flat detector 104. According to some embodiments of the present invention, an additional ring of x-ray absorbing material (not shown) may be placed around the imaging device 104 to further enhance radiation shielding.

Stepwise Implementation

When the system 100 is implemented using an existing c-arm, the success of the gantry 300 design may be verified by starting the configuration with a source to image distance identical to the original c-arm, according to embodiments of the present invention. This may permit use of all original modes of operation, such as, for example, the 30 fr/s pulsed fluoroscopy mode, but now with improved freedom of movement. Once the alignment mechanism is verified to work properly, the variable source to image distance portion of the design may be implemented. With the beam-centering mechanism in place and tested, the beam 504 for each source to image distance may be appropriately collimated to ensure that the beam 504 does not exceed the imaging surface of the imaging device 104. The implementation of this step may depend somewhat on the collimation capabilities of the fluoroscopy units used.

If necessary, the user may allow only a series of discreet SIDs clearly marked on the positioning frame 502 or bar 602 (e.g., using drill holes for fixation with engraved SID marking) according to embodiments of the present invention. For each of the discreet SIDs, a fixed collimator may be attached to the x-ray generator 102 that is accurately calibrated for that specific source to image distance. If the purchased fluoroscopy units provide sophisticated collimation options (e.g., stepless collimation), such sophisticated collimation options may be used instead of the removable, fixed-aperture, beam-limiting devices. According to some embodiments of the present invention, source to image distance changes will rarely occur. Based on studies in the literature, a source to image distance of 1.5 to 1.75 meters is a desirable setup for lower extremity studies.

Imaging Improvements

According to some embodiments of the present invention, the imaging system of the c-arm fluoroscopy units may be upgraded with respect to their original imaging systems. According to some embodiments of the present invention, the upgrade may be implemented such that the original optics for the imaging system can be periodically reattached to make the pulsed fluoroscopy mode available when desired. For the upgrade, the existing optical system (lenses and camera assembly) that records the images from the light-emitting screen on the back of the image intensifier 104 may be removed, and replaced with a new optical recording system.

Figures 10A, 10B:
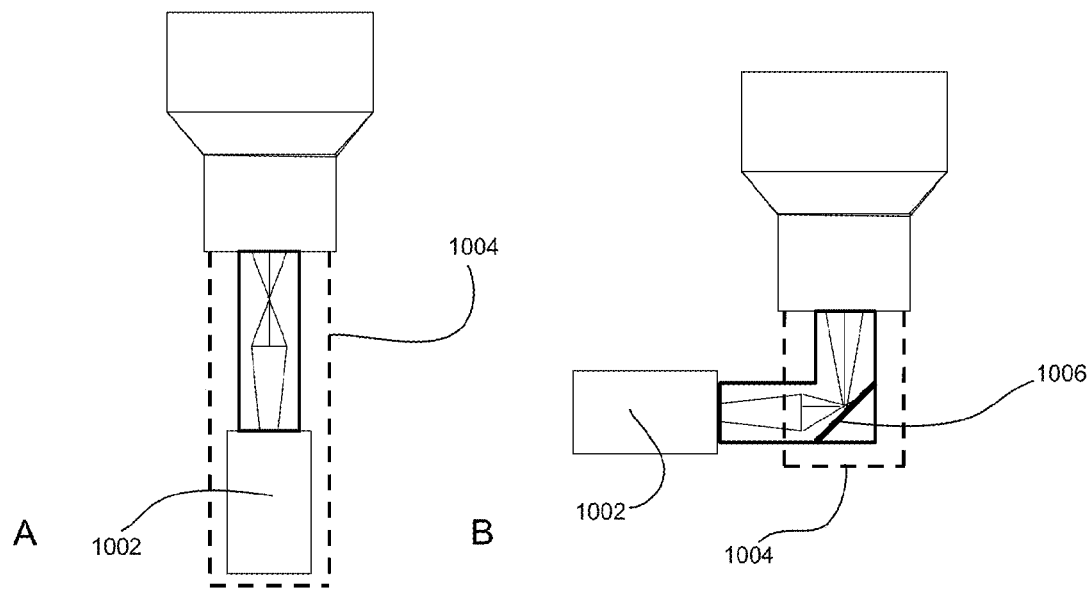
FIGS. 10A and 10B illustrate a top view schematics for new replacement optics and high-speed camera, according to embodiments of the present invention.

Various designs for the new optical recording system are contemplated, according to embodiments of the present invention. For example, one such design may employ a high-speed camera assembly 1002 with a microtable for focusing and a bellow to block any outside lighting as well as leakage radiation. FIGS. 10A and 10B illustrate top view schematic designs for new replacement optics and a high-speed camera 1002. FIG. 10A illustrates a simpler optics design, but further enhanced modifications may serve to block any radiation coming through the image intensifier. FIG. 10B illustrates an optics design that includes a mirror, but that may simplify radiation shielding.

Figure 11:
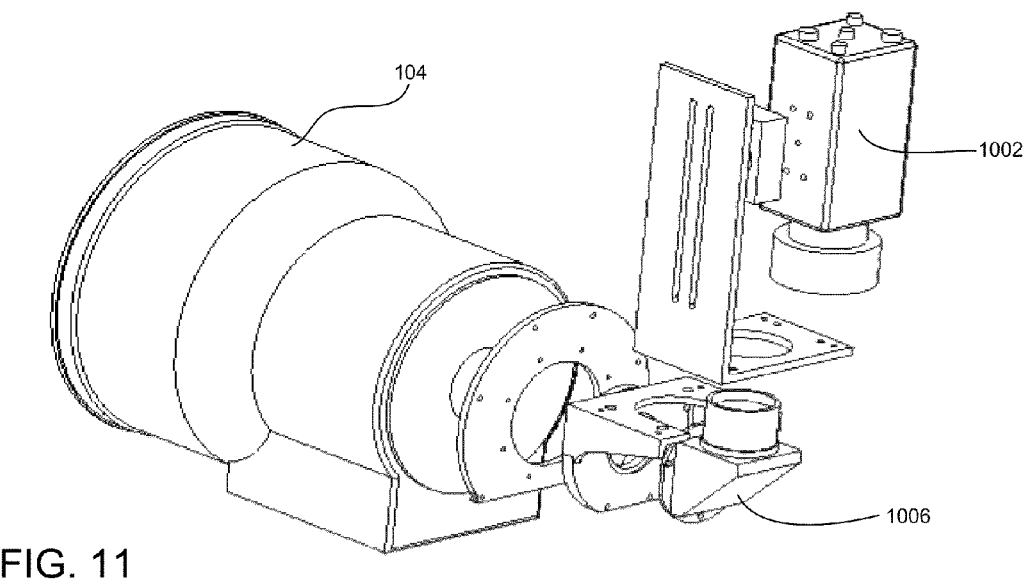
FIG. 11 illustrates a perspective exploded view of optical system coupling hardware which facilitates attachment and detachment of a camera with an image intensifier, according to embodiments of the present invention.
Figure 12:
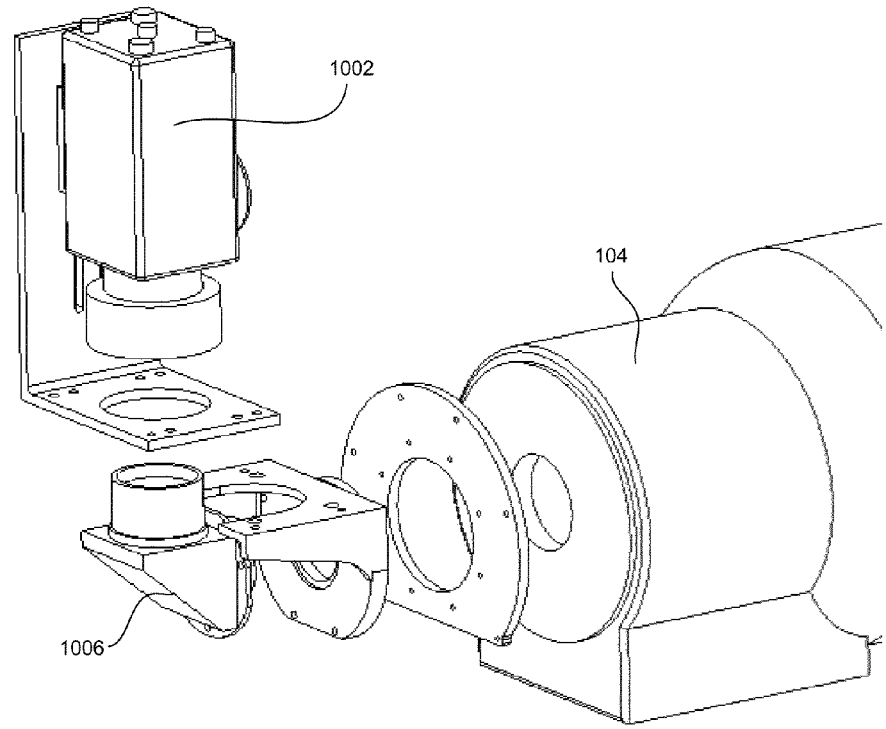
FIG. 12 illustrates an alternative perspective exploded view of the optical system coupling hardware of FIG. 11, according to embodiments of the present invention.

Embodiments of the present invention may be encapsulated with x-ray absorbing material 1004 to comply with potentially applicable x-ray leakage requirements. Because such encapsulation may increase the bulk of the system, a second example design for a new optical recording system includes a mirror 1006 that would put the camera assembly 1002 at a ninety degree angle with respect to the image intensifier 104, as illustrated in FIG. 10B. Such an angled 'bellow' would be the only portion to be encapsulated with x-ray absorbing material 1004, according to embodiments of the present invention. FIGS. 11 and 12 illustrate optical system coupling hardware which facilitates attachment and detachment of the camera 1002 with the image intensifier 104.

Operational Consequences

For some c-arm fluoroscopic models, the removal of the existing optical system may disable existing fluoroscopy functionality, unless manual modes are available, because image information may be used in various feedback loops that control the technique factors in fluoroscopic mode. For some fluoroscopy systems, the existing optical system may need to remain electrically connected because some fluoroscopy units may not operate at all when the optical system is disconnected. Often, the radiographic mode of such systems remains operable, however, because this mode does not require image feedback. Therefore, according to some embodiments of the present invention, fluoroscopy components of a dual fluoroscopy system may be operated in radiographic mode while the new optical recording system records the images. Such a configuration, according to embodiments of the present invention, effectively becomes a radiographic system. Another benefit to operating embodiments of the system in radiographic mode is that the high-speed camera 1002 with its high shutter speed operates with output images with much higher intensity compared to the existing optical system, according to embodiments of the present invention. This calls for increased technique factors that may exceed fluoroscopic-mode entrance dose limits, but that may be common in radiographic mode.

Because embodiments of a dual fluoroscopy system for joint motion measurement may be used to record information about short and fast events, an exemplary maximum of 1.0 to 2.0 second exposures may be enough to obtain useful information given the speed of the motion and the relatively small viewing volume of the system, according to some embodiments of the present invention. Minimization of subject risk may be achieved by carefully controlling the duration of each exposure and significantly limiting the number of exposures for each subject, according to embodiments of the present invention.

Triggering and Beam Visualization Device

A triggering and beam visualization device, according to embodiments of the present invention, permits the biplane fluoroscopy system to generate x-rays only when: (1) a manual switch is pressed, (2) alignment photocells 802 indicate the biplane fluoroscopy system is properly aligned, and (3) signals from sensors attached to the subject (e.g., accelerometers, goniometers, etc.) or contacted by the subject (e.g., force plates, pressure sensors, photocells) trigger the exposure. In addition, the x-ray generator may be configured to stop exposure after a preset duration or second control event, according to embodiments of the present invention. A multi-laser device may be attached to the generator 102 to show the field of view 108 of each of the two fluoroscopy units and to provide visual feedback that the device is active. Such a visual indicator may be removably attached to the x-ray generator 102, according to embodiments of the present invention. Such a device may also have the capability to activate the lasers and/or other light source without activating the fluoroscopy system, in order to permit timing verification and subject training prior to x-ray exposure, according to embodiments of the present invention.

Triggering Device

Other potentially applicable government regulations may specify that the fluoroscopy system can in no way produce x-rays without one of the two buttons on the control switch being pressed by an operator. Such a configuration may prevent any accidental signals produced by the triggering device while being switched on or off or while connecting the switch or any of the sensors. In addition, other potentially applicable government regulations may specify that the fluoroscopy system can in no way produce x-rays unless the x-ray generator 102 and the imaging device 104 are properly positioned (e.g., the x-ray beam is centered on the imaging device 104 within 2% of the source to image distance (2 cm for SIDs greater than or equal to 100 cm)) so that the imaging device properly serves as the primary barrier. That is, the x-ray beam is perpendicular to and aimed at the center of the imaging device 104 as described above, according to embodiments of the present invention. Since the generator 102 and imaging device 104 will be on separate movable towers, according to embodiments of the present invention, photocells 804 or other positional sensors may be used to ensure proper positioning and alignment. The signals from the photocells 802 or positional sensors may be used to ensure that x-rays can be produced only when the components are positioned properly (e.g., better than 1 cm from the ideal position), according to embodiments of the present invention.

Figure 17:
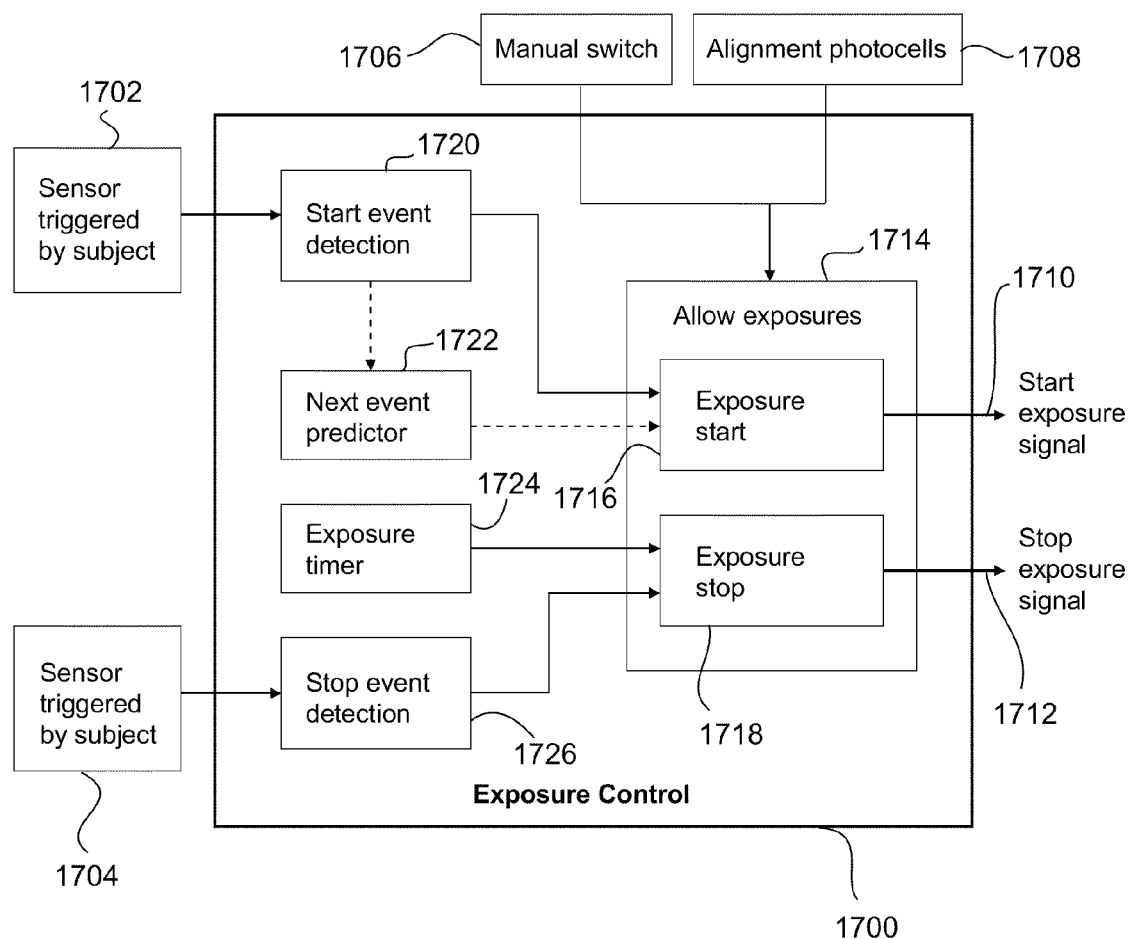
FIG. 17 illustrates an exposure control module flow chart, according to embodiments of the present invention.

FIG. 17 illustrates an exposure control module 1700 flow diagram, according to embodiments of the present invention. The exposure control module 1700 may be implemented in hardware, in software on a computer system, or a combination of both, according to embodiments of the present invention. The exposure control module 1700 receives signals from various sensors 1702, 1704 which are capable of being triggered by a subject or a patient, according to embodiments of the present invention. Sensors 1702, 1704 may be motion sensors, for example. The exposure control module 1700 may also receive signals from a manual switch 1706 and/or one or more alignment photocells 1708, according to embodiments of the present invention. Exposure control module 1700 controls the start signal 1710 and the stop signal 1712 which define the duration for each x-ray generator 102 radiation exposure, according to embodiments of the present invention.

An exposure allowance module 1714 includes an exposure start submodule 1716 configured to send the start exposure signal 1710 at the appropriate time and an exposure stop submodule 1718 configured to send the stop exposure signal 1712 at the appropriate time, according to embodiments of the present invention. According to some embodiments of the present invention, the exposure allowance module 1714 monitors the activation signals from the manual switch 1706 and/or the one or more alignment photocells 1708 and prevents the exposure start module 1716 from sending the start exposure signal 1710 unless the manual switch 1706 is activated and/or the one or more alignment photocells 1708 indicate alignment. According to other embodiments of the present invention, the exposure allowance module 1714 monitors the activation signals from the manual switch 1706 and/or the one or more alignment photocells 1708 and immediately instructs the exposure stop module 1718 to send the stop exposure signal 1712 if the manual switch 1706 signal is de-activated and/or the alignment photocells 1708 indicate misalignment.

An event start detection module may receive a trigger signal from sensor 1702 and instruct the exposure start submodule 1716 to send the start exposure signal 1710, according to embodiments of the present invention. Alternatively, a next event prediction module 1722 may note the triggering of sensor 1702 and, based on observed or stored data, predict when the next even of interest will occur and instruct the exposure start submodule 1716 to send the start exposure signal 1710 accordingly.

According to some embodiments of the present invention, the timing of the stop exposure signal 1712 may be determined by an exposure timer module which begins a timer when the start exposure signal 1710 is sent and instructs the exposure stop submodule 1718 to send the stop exposure signal 1712 when the timer count reaches a predetermined count. According to other embodiments of the present invention, a stop event detection module 1726 receives a signal from another trigger 1704 and, in response, instructs the exposure stop module 1718 to send the stop exposure signal 1712. Stop event detection module 1726 may also be configured to monitor a subsequent signal from the same sensor 1702 which initiated the start of the exposure, according to embodiments of the present invention. According to some embodiments of the present invention, the start exposure signal 1710 and/or the stop exposure signal 1712 may constitute the triggering signal 1304 of FIG. 14, which is passed to the system control modules 1302, 1402 to control the synchronized exposure of two x-ray generators 102. Based on the disclosure provided herein, one of ordinary skill in the art will appreciate the different sensors that may be employed as well as the different ways the start and stop of the radiation exposure may be controlled.

Minimizing the dose to the patient is a significant safety consideration in the use of radiation. Image quality determines the x-ray energy and power characteristics, which leaves beam-on duration as the primary control mechanism to be minimized. Sensors 1702, 1704 can be used to detect the motion of interest. Allowing sensors 1702, 1704 to trigger the exposure control module 1700 may eliminate the need to start radiation production manually and a little early, as is typically done to make sure the motion of interest is recorded. Similarly, being able to accurately set the duration of the radiation exposure or to stop it when the motion of interest has been completed based on a sensor may minimize radiation exposure as well. Two types of sensors may be used, for example, according to embodiments of the present invention: binary and analog. Binary sensors such as photocells 802 may be allowed to go to both High and Low states to trigger the x-ray generator 102. One simple way to use analog signals to trigger the x-ray generator 102 is to be able to set a threshold voltage to trigger the system (again, both rising above and dropping below the threshold). This threshold may be variable to permit individualization to the patient and to a particular sensor.

In addition, the duration of the radiation exposure from the x-ray generator may be limited electronically, according to embodiments of the present invention. For example, each x-ray exposure from the x-ray generator 102 may be configured to last only until an additional sensor signal is received, either from the same motion sensor 1702 used to trigger the x-ray generation or from another sensor 1704. Alternatively, a timer (e.g. timer module 1724) may be used to limit the duration of each exposure, according to embodiments of the present invention.

Many events to be imaged by biplane fluoroscopy systems according to embodiments of the present invention are cyclic. Therefore, a triggering system with a next event predictor module 1722 that is capable of determining and subsequently predicting the next event (e.g., entrainment) may be used, according to embodiments of the present invention. For instance, a pressure sensor 1702 attached to a shoe can be used to detect heel strikes for a subject walking on a treadmill; EKG signals can be used to detect heart beats, etc. After a number of heel strikes, the control module 1700 may be configured to predict the next heel strike event with reasonable accuracy. This information can then be used to trigger the system with a certain amount of prediction or delay relative to the predicted next heel strike, according to embodiments of the present invention.

Visualization Device

Figure 16:
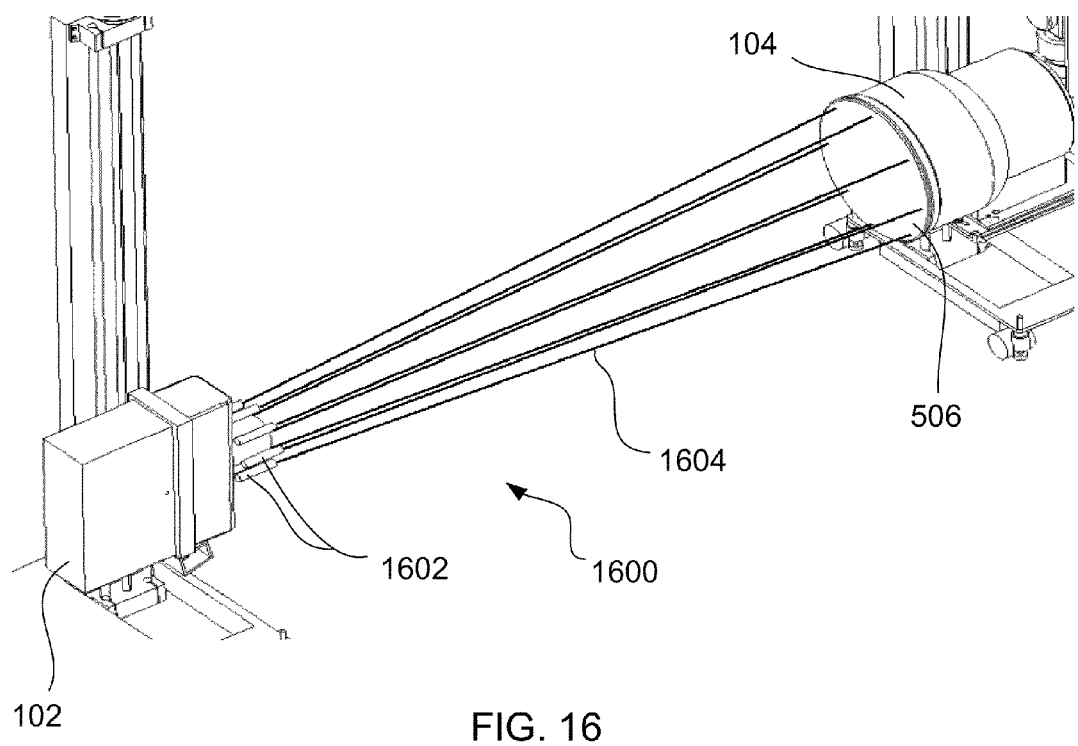
FIG. 16 illustrates a beam visualization device, according to embodiments of the present invention.

FIG. 16 illustrates a beam visualization device 1600 applied to one of the x-ray generators 102, according to embodiments of the present invention. Visualization of both the on-time and the field of view of the x-ray generator 102 are helpful during preparation. For instance, such information may be used to determine whether the object of interest will be in the field of view during the radiation exposure. Or such information may be used to determine whether the sensor threshold or photocell position is set appropriately to time the radiation exposure correctly. Since the device 1600 is preferably positioned to stay out of the x-ray beam, a ring of laser pointers 1602 (eight to ten, for example) may be attached to the two x-ray generators 102, according to embodiments of the present invention. To identify each generator 102, two laser colors may be used. The lasers may be easily detachable and easy to align with the field of view 108, which will vary with the variation of the source to image distance. The lasers produce beams 1604 which, in the absence of an object between the x-ray generator 102 and the imaging device 104, contact the imaging surface 506 of the imaging device 104, according to embodiments of the present invention. The two laser systems may also be configured to operate both simultaneously and separate from each other as well as simultaneously or separate from the fluoroscopy system 100, according to embodiments of the present invention. Based on the disclosure provided herein, one of ordinary skill in the art will recognize the various ways in which lasers 1602 may be pointed and/or oriented to provide a visualization of the field of view 108.

Accurate and Flexible Calibration Method

In order to reconstruct the location and motion of an object imaged and recorded by the above described biplane fluoroscopy system 100, it is desirable to measure and correct the image distortion of the imaging system 104 as well as determine the geometric configuration of the fluoroscopy system 100, including the three-dimensional location of the focal spot of each x-ray generator 102; direction of each x-ray beam 504; and location and orientation of each imaging surface 506, according to embodiments of the present invention. This may be achieved by first imaging a flat plate attached to the surface 506 of the imaging device 104. The flat plate may be constructed of a material which is relatively opaque with respect to x-rays, with rows and columns of holes of known dimensions Alternatively, a transparent flat plate with opaque markers attached may be used. The positions of the holes or markers in the images can then be used to correct any distortions and to provide a distance measure to the pixels of the images (e.g., 0.01 mm/pixel), according to embodiments of the present invention.

Next a transparent box adequately sized for the viewing volume of interest with a minimum of 6 radio-opaque markers viewable by both fluoroscopy units may be imaged, according to embodiments of the present invention. First the location of the x-ray focal spot relative to the imaging device 104 can be calculated for each fluoroscopy system independently. Such a method for calculating the location of the x-ray focal spot relative to the imaging device 104 comprises of two nested optimization loops and the following steps, according to embodiments of the present invention:

1. identify the markers of the box in the (distortion corrected) image and determine their locations in the image plane, 2. choose the initial positions of the box and focus position (arbitrarily or via user feedback),
3. initiate an inner optimization loop which finds the location of the box that has the lowest error (best match) comprising of the following steps:
   A. for every marker calculate the projection line from focus position to the marker location in the image plane,
   B. calculate the shortest distance between each projection line and marker based on the box position,
   C. using optimization algorithms (e.g., quadratic programming, simulated annealing), find the position of the box that minimizes the average distance for all markers (matching error), and
4. using optimization algorithms (e.g., quadratic programming, simulated annealing), initiate the outer optimization loop which finds the focus position that produces the lowest matching error found by running the inner optimization loop at every step.

Alternatively, the following method for calculating the location of the x-ray focal spot relative to the imaging device 104 can be used, according to embodiments of the present invention:

1. identify the markers of the box in the (corrected) image and determine their locations in the image plane,
2. choose the initial position of the box (arbitrarily or via user feedback) and for every marker calculate the projection line from the marker location in the image plane through the marker location of the box in space to infinity (project away from the image plan toward the x-ray focal point),
3. calculate the shortest distance between the projection lines,
4. using optimization algorithms (e.g., quadratic programming, simulated annealing), minimize the distances between the projection lines by adjusting the location and orientation of the box (should near zero), and
5. locating the x-ray focal point by locating the intersection of the projection lines.

Subsequently, the location of the image planes and the foci of the two fluoroscopy systems relative to each other can be determined using established algorithms such as the direct linear transformation (DLT) algorithm and its many variations. Based on the disclosure provided herein, one of ordinary skill in the art will appreciate the various ways in which the system 100 may be accurately calibrated.

X-Ray Generator Upgrade (Modification Implementation)

According to some embodiments of the present invention, no further changes are needed to the x-ray generation system 102 to effectively measure joint motion. However, some fluoroscopy units have lower x-ray generator power (e.g., kW) compared to film radiographic units and in some cases desired technique factors may fall toward the high end of the available ranges. According to some embodiments of the present invention, where the x-ray generators 102 of the fluoroscopy units do not generate a sufficient amount and/or duration of radiation to produce images of appropriate quality for analysis, then the x-ray generators 102 of the dual fluoroscopy system may be upgraded. In such cases, certified radiographic x-ray generators 102 may be used to replace the existing x-ray generators 102. According to some embodiments of the present invention, and depending upon the baseline fluoroscopy systems employed, replacing the existing x-ray generators 102 may eliminate the possibility of returning back to a 30 fr/s pulsed fluoroscopy mode and may render the resulting system a strictly radiographic system.

Figure 15:
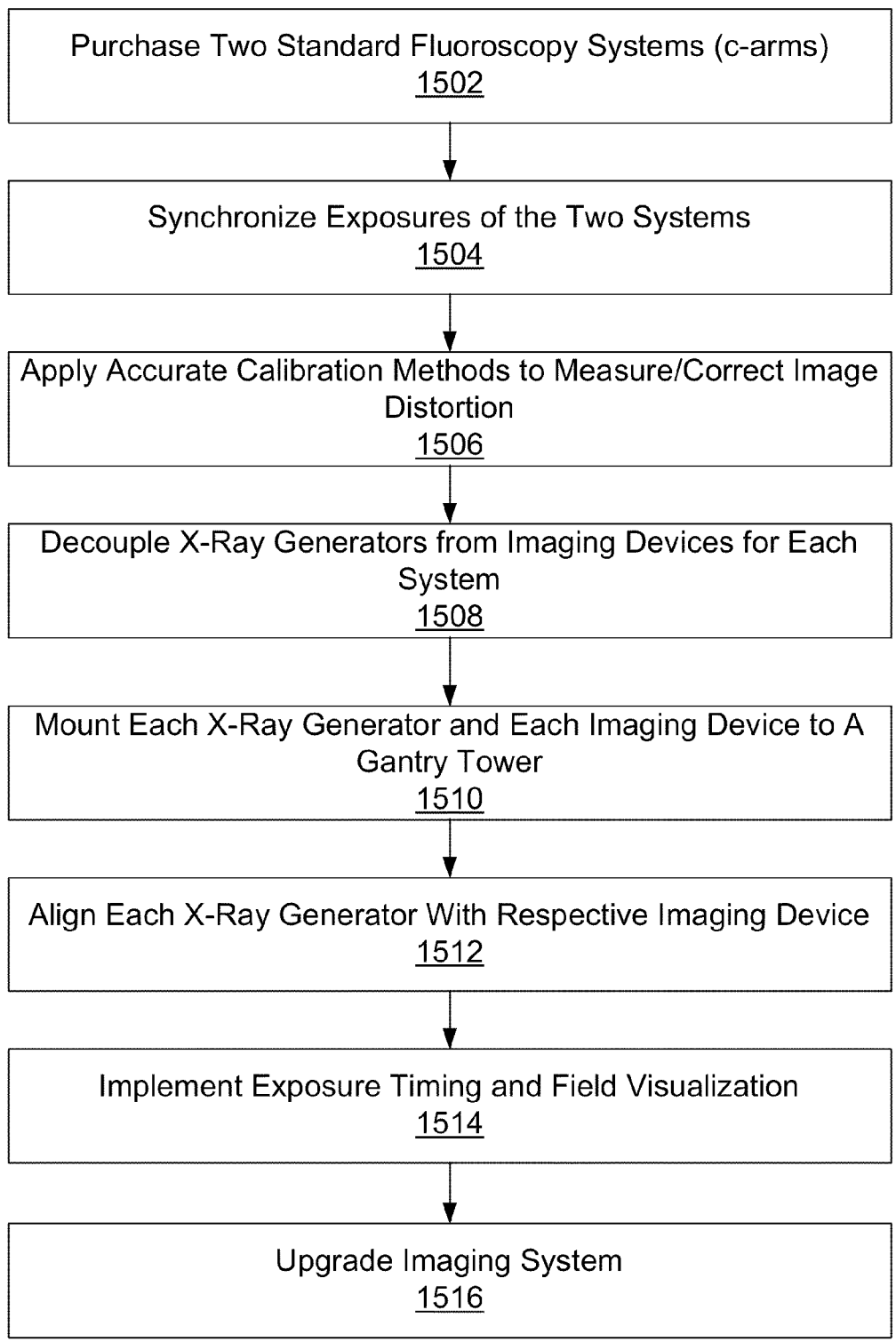
FIG. 15 depicts a flow chart illustrating a method for constructing dual fluoroscopy systems, according to embodiments of the present invention.

FIG. 15 depicts a flow diagram 1500 illustrating methods for constructing a dual fluoroscopy system, according to embodiments of the present invention. First, two standard c-arm fluoroscopy systems may be purchased (block 1502). Each c-arm includes an x-ray generator 102 and an imaging device 104, such as an image intensifier, according to embodiments of the present invention. The exposures of the two systems may be synchronized as described above (block 1504). One or more accurate calibration methods may be applied to measure and/or correct image distortion, as well as determine the geometric configuration of the dual fluoroscopy system, as described above (block 1506). The x-ray generators 102 and imaging devices 104 may be decoupled from their c-arms (block 1508) and mounted to their own gantry towers (block 1510) as described above. Each x-ray generator 102 is aligned with its respective imaging device (block 1512), according to embodiments of the present invention. According to some embodiments of the present invention, an exposure timing and field visualization system may be implemented (block 1514). The imaging system of the imaging devices 104 may also be upgraded to include cameras or other devices with higher frame and/or data capture rates, according to embodiments of the present invention (block 1516). For example, a frame rate of 250 frames per second or higher may be used, according to embodiments of the present invention. The existing camera of the imaging device 104 may be replaced with a Vision Research Phantom v5.1 1024×1024 pixel 1200 frames per second high speed camera, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for constructing a dual fluoroscopy system, comprising:
   providing a first c-arm and a second c-arm, wherein the first c-arm comprises a first x-ray generator and a first imaging device, and wherein the second c-arm comprises a second x-ray generator and a second imaging device;
   synchronizing exposure timing of the first x-ray generator and the second x-ray generator;
   decoupling the first x-ray generator and the first imaging device from the first c-arm and the second x-ray generator and the second imaging device from the second c-arm;
   mounting the first and second x-ray generators and the first and second imaging devices to a gantry system;
   aligning the first x-ray generator with the first imaging device and aligning the second x-ray generator with the second imaging device; and
   performing a calibration test to determine three-dimensional positions and orientations of the first and second x-ray generators and the first and second imaging devices.

2. The method of claim 1, wherein the gantry system comprises first, second, third, and fourth gantries, the method further comprising:
   mounting the first x-ray generator to the first gantry, the second x-ray generator to the second gantry, the first imaging device to the third gantry, and the second imaging device to the fourth gantry.

3. The method of claim 2, wherein aligning the first x-ray generator with the first imaging device comprises aligning the first gantry with the third gantry using an alignment frame.

4. The method of claim 1, wherein synchronizing the exposure timing of the first x-ray generator and the second x-ray generator comprises making the exposure timing of the first x-ray generator and the second x-ray generator to be simultaneous.

5. The method of claim 1, wherein synchronizing the exposure timing of the first x-ray generator and the second x-ray generator comprises pulsing the exposure of the first x-ray generator out of phase with pulsing the exposure of the second x-ray generator.

6. The method of claim 1, further comprising:
projecting from the first x-ray generator a visual indication of at least a portion of a field of view of the first x-ray generator.

7. The method of claim 6, wherein projecting from the first x-ray generator the visual indication of at least a portion of the field of view of the first x-ray generator comprises attaching three or more laser generation devices to a perimeter of the first x-ray generator.

8. The method of claim 7, wherein the three or more laser generation devices are a first set of three or more laser generation devices, the method further comprising attaching a second set of three or more laser generation devices to a perimeter of the second x-ray generator.

9. The method of claim 8, wherein the first set of three or more laser generation devices produce lasers of a first color, and wherein the second set of three or more laser generation devices produce lasers of a second color different from the first color.

10. The method of claim 6, wherein a duration of the visual indication is configured to correspond with the exposure timing of the first x-ray generator.

11. The method of claim 1, wherein performing a calibration test of the first and second x-ray generators comprises locating in three dimensions a focal spot of the first and second x-ray generators.

12. The method of claim 1, wherein performing a calibration test of the first and second x-ray generators comprises locating in three dimensions a beam direction of the first and second imaging devices.

13. The method of claim 1, wherein performing a calibration test of the first and second x-ray generators comprises locating in three dimensions a location and orientation of the first and second imaging devices.

14. The method of claim 1, wherein the first imaging device includes a first existing optical system, and wherein the second imaging device includes a second existing optical system, the method further comprising:
removing the first existing optical system from the first imaging device and the second existing optical system from the second imaging device; and
installing a first new optical system into the first imaging device and a second new optical system into the second imaging device,
wherein a frame capture rate capability of the first and second new optical systems is higher than a frame capture rate capability of the first and second existing optical systems.

15. The method of claim 14, wherein the first imaging device includes a first camera assembly, and wherein an optical axis of the first camera assembly is substantially perpendicular to an optical axis of the first imaging device.

16. The method of claim 1, further comprising:
electrically coupling a manual switch with the first x-ray generator and the second x-ray generator; and
generating x-rays with the first x-ray generator and the second x-ray generator only when the manual switch is activated.

17. The method of claim 1, further comprising:
detecting motion of a subject with a motion sensor; and
generating x-rays with the first x-ray generator and the second x-ray generator only when the motion sensor is activated.

18. The method of claim 17, wherein the first x-ray generator and the second x-ray generator generate x-rays for a duration determined by a timer or by input from another sensor.

19. The method of claim 1, further comprising:
affixing a first photocell to one of the first x-ray generator or the first imaging device;
affixing a first reflector to the other of the first x-ray generator or the first imaging device;
affixing a second photocell to one of the second x-ray generator or the second imaging device;
affixing a second reflector to the other of the second x-ray generator or the second imaging device;
generating x-rays with the first x-ray generator and the second x-ray generator only when the first photocell is aligned with the first reflector and the second photocell is aligned with the second reflector.

20. The method of claim 1, further comprising:
affixing a first laser to one of the first x-ray generator or the first imaging device;
affixing a first photodiode to the other of the first x-ray generator or the first imaging device;
affixing a second laser to one of the second x-ray generator or the second imaging device;
affixing a second photodiode to the other of the second x-ray generator or the second imaging device;
generating x-rays with the first x-ray generator and the second x-ray generator only when the first laser is aligned with the first photodiode and the second laser is aligned with the second photodiode.

21. The method of claim 1, further comprising:
electrically coupling a manual switch with the first x-ray generator and the second x-ray generator;
detecting motion of a subject with a motion sensor;
affixing a first laser to one of the first x-ray generator or the first imaging device;
affixing a first photodiode to the other of the first x-ray generator or the first imaging device;
affixing a second laser to one of the second x-ray generator or the second imaging device;
affixing a second photodiode to the other of the second x-ray generator or the second imaging device; and
generating x-rays with the first x-ray generator and the second x-ray generator only when: the manual switch and the motion sensor are activated and the first laser is aligned with the first photodiode and the second laser is aligned with the second photodiode.

22. The method of claim 1, wherein aligning the first x-ray generator with the first imaging device comprises connecting the first x-ray generator with the first imaging device by an alignment bar.

23. The method of claim 1, wherein the first imaging device includes a first camera assembly, and wherein an optical axis of the first camera assembly is substantially perpendicular to an optical axis of the first imaging device.

24. A method for constructing a dual fluoroscopy system, comprising:
- providing a first c-arm and a second c-arm, wherein the first c-arm comprises a first x-ray generator and a first imaging device, wherein the second c-arm comprises a second x-ray generator and a second imaging device, and wherein the first and second c-arms have a first source-to-image distance;
- decoupling the first x-ray generator and the first imaging device from the first c-arm and the second x-ray generator and the second imaging device from the second c-arm;
- mounting the first x-ray generator to a first gantry, the second x-ray generator to a second gantry, the first imaging device to a third gantry, and the second imaging device to a fourth gantry;
- aligning the first x-ray generator with the first imaging device and aligning the second x-ray generator with the second imaging device;
- synchronizing exposure timing of the first x-ray generator and the second x-ray generator;
- performing a calibration test of the first and second x-ray generators to measure and correct image distortion; and
- vertically adjusting a height of the first and second x-ray generator and of the first and second imaging devices to image a particular area of a patient's body.

25. The method of claim 24, wherein the particular area is a shoulder.

26. The method of claim 24, wherein the particular area is a knee.

* * * * *